US010485628B2

(12) United States Patent
Gallagher et al.

(10) Patent No.: US 10,485,628 B2
(45) Date of Patent: Nov. 26, 2019

(54) SLIP CARD FOR LONG SEALED TRAYS AND METHOD

(71) Applicant: Medtronic Vascular, Inc., Santa Rosa, CA (US)

(72) Inventors: John Gallagher, Galway (IE); David Clarke, Galway (IE); Raymond Ryan, Limerick (IE); Jeffrey Barnell, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 72 days.

(21) Appl. No.: 15/333,317

(22) Filed: Oct. 25, 2016

(65) Prior Publication Data

US 2018/0008363 A1    Jan. 11, 2018

Related U.S. Application Data

(60) Provisional application No. 62/359,049, filed on Jul. 6, 2016.

(51) Int. Cl.
*A61B 50/36* (2016.01)
*A61B 50/33* (2016.01)
(Continued)

(52) U.S. Cl.
CPC ........ *A61B 50/36* (2016.02); *A61B 17/00234* (2013.01); *A61B 50/33* (2016.02);
(Continued)

(58) Field of Classification Search
CPC ...... B65D 1/40; B65D 43/02; B65D 73/0021; B65D 73/0085; A61B 50/30; A61B 50/33; A61B 2050/0065
(Continued)

(56) References Cited

U.S. PATENT DOCUMENTS 4,482,053 A * 11/1984 Alpern ...................... A61L 2/26
   206/439
4,750,619 A *  6/1988 Cohen ................... A61F 2/0095
   206/363

(Continued)

FOREIGN PATENT DOCUMENTS

EP       2106821 A1     10/2009
EP       2468346 A1      6/2012
(Continued)

OTHER PUBLICATIONS

PCT/US2017/040050, The International Search Report and the Written Opinion of the International Searching Authority, dated Sep. 29, 2017, 12pgs.

(Continued)

*Primary Examiner* — J. Gregory Pickett
*Assistant Examiner* — Brijesh V. Patel (57) ABSTRACT

A delivery system package includes a tray, a delivery system, and a slip card between the tray and the delivery system. To remove the delivery system, a pull tab of the slip card is moved to raise the slip card including the delivery system from the tray. At the same time, this moves the slip card over a lid sealing flange of the tray, considered a non-sterile surface in accordance one embodiment. Accordingly, the slip card extends over the lid sealing flange preventing contact between the delivery system and the lid sealing flange. In addition, the slip card effectively forms a ramp for sterile removal of the delivery system from the tray.

11 Claims, 12 Drawing Sheets

(51) Int. Cl.
| | |
|---|---|
| *A61B 17/00* | (2006.01) |
| *A61F 2/95* | (2013.01) |
| *B65B 7/02* | (2006.01) |
| *B65D 1/34* | (2006.01) |
| *A61F 2/00* | (2006.01) |
| *A61M 25/00* | (2006.01) |
| *B65D 25/10* | (2006.01) |
| *B65D 43/02* | (2006.01) |
| *A61B 50/30* | (2016.01) |
| *A61L 2/20* | (2006.01) |

(52) U.S. Cl.
CPC .............. *A61F 2/0095* (2013.01); *A61F 2/95* (2013.01); *A61M 25/002* (2013.01); *B65B 7/02* (2013.01); *B65D 1/34* (2013.01); *B65D 25/10* (2013.01); *B65D 25/105* (2013.01); *B65D 43/0202* (2013.01); *H05K 999/99* (2013.01); *A61B 2017/00362* (2013.01); *A61B 2050/314* (2016.02); *A61L 2/206* (2013.01)

(58) Field of Classification Search
USPC ........ 206/363–364, 370, 438–439; 220/23.9, 220/359.4; 229/126–128, 155
See application file for complete search history.

(56) References Cited

U.S. PATENT DOCUMENTS

| | | | |
|---|---|---|---|
| 5,090,571 A | 2/1992 | Walker | |
| 5,131,537 A * | 7/1992 | Gonzalez | A61M 25/002 206/364 |
| 5,246,109 A * | 9/1993 | Markle | A61B 5/145 206/363 |
| 5,322,163 A * | 6/1994 | Foos | A61M 25/002 206/364 |
| 5,351,822 A * | 10/1994 | Sinn | A61B 17/06138 206/363 |
| 5,379,895 A * | 1/1995 | Foslien | A61B 50/30 206/363 |
| 5,392,918 A * | 2/1995 | Harrison | A61M 25/002 206/364 |
| 5,407,070 A * | 4/1995 | Bascos | A61M 5/002 206/364 |
| 5,601,189 A * | 2/1997 | Roshdy | B65D 73/0021 206/363 |
| 5,699,909 A * | 12/1997 | Foster | B65D 77/26 206/370 |
| 5,758,775 A * | 6/1998 | Lowe | A61M 5/3205 206/364 |
| 5,772,031 A * | 6/1998 | Landis | A61B 50/30 206/363 |
| 5,788,063 A * | 8/1998 | Van Ness | A61B 17/06138 206/380 |
| 5,842,567 A * | 12/1998 | Rowe | A61B 50/3001 206/364 |
| 2003/0121821 A1 | 7/2003 | Roshdy | |
| 2005/0033430 A1* | 2/2005 | Powers | A61B 17/7059 623/17.11 |
| 2005/0085834 A1* | 4/2005 | Carranza | A61B 50/30 606/153 |
| 2007/0074990 A1* | 4/2007 | Merboth | A01N 1/02 206/438 |
| 2011/0155608 A1 | 6/2011 | Foster | |
| 2012/0305441 A1 | 12/2012 | Murray et al. | |
| 2015/0068939 A1 | 3/2015 | Seitz, III | |

FOREIGN PATENT DOCUMENTS

| | | |
|---|---|---|
| EP | 2609955 A1 | 7/2013 |
| EP | 2609956 A1 | 7/2013 |
| JP | 2011139882 A | 7/2011 |
| WO | 96/39340 A1 | 12/1996 |
| WO | 02/47602 A2 | 6/2002 |
| WO | 2002/47602 A2 | 6/2002 |
| WO | 2005/092419 A1 | 10/2005 |
| WO | 2015/089197 A2 | 6/2015 |

OTHER PUBLICATIONS

U.S. Appl. No. 62/359,049, of Jeffrey Barnell, titled "Hybrid Sealed Tray for Long Atheter Delivery Systems", filed Jul. 6, 2016.
U.S. Appl. No. 15/277,509, of Jeffrey Barnell, titled "Hybrid Sealed Tray for Long Catheter Delivery Systems", filed Sep. 27, 2016.
U.S. Appl. No. 15/271,537, of Jeffrey Barnell, titled "Biomatter Capture Mechanism and Method", filed Sep. 27, 2016.
U.S. Appl. No. 15/332,968, of Jeffrey Barnell et al., titled "Device Retention Mechanism and Method", filed Oct. 24, 2016.
U.S. Appl. No. 15/333,287, of John Gallagher, titled "Hinged Long Sealed Tray and Method", filed Oct. 25, 2016.
PCT/US2017/040587, The International Search Report and the Written Opinion of the International Searching Authority, dated Sep. 29, 2017, 13 pages.
PCT/US2017/040590, The International Search Report and the Written Opinion of the International Searching Authority, dated Sep. 29, 2017, 15 pages.

* cited by examiner

SLIP CARD FOR LONG SEALED TRAYS AND METHOD

RELATED APPLICATIONS

This application claims the benefit of U.S. Provisional Application No. 62/359,049 filed on Jul. 6, 2016, entitled "HYBRID SEALED TRAY FOR LONG CATHETER DELIVERY SYSTEMS" of Jeffrey Barnell, which is incorporated herein by reference in its entirety.

BACKGROUND

Field

The present application relates to packaging for an intra-vascular device and method. More particularly, the present application relates to packaging for a device for treatment of intra-vascular diseases and related methods.

Description of the Related Art

Long catheter delivery systems, e.g., one meter or greater in length, present challenges in sterile removal and aseptic presentation from the delivery system package. Specifically, the delivery system must be removed from the sterile barrier package without contacting non-sterile surfaces of the protective package.

SUMMARY

In accordance with one embodiment, a delivery system package includes a tray, a delivery system, and a slip card between the tray and the delivery system. To remove the delivery system, e.g., an inner tray containing the delivery system, a pull tab of the slip card is moved to raise the slip card including the delivery system from the tray. At the same time, this moves the slip card over a lid sealing flange of the tray, considered a non-sterile surface in accordance one embodiment. Accordingly, the slip card extends over the lid sealing flange preventing contact between the delivery system and the lid sealing flange. In addition, the slip card effectively forms a ramp for sterile removal of the delivery system from the tray.

These and other features in accordance with various embodiments will be more readily apparent from the detailed description set forth below taken in conjunction with the accompanying drawings.

BRIEF DESCRIPTION OF DRAWINGS

Common reference numerals are used throughout the drawings and detailed description to indicate like elements.

DETAILED DESCRIPTION

Figure 1:
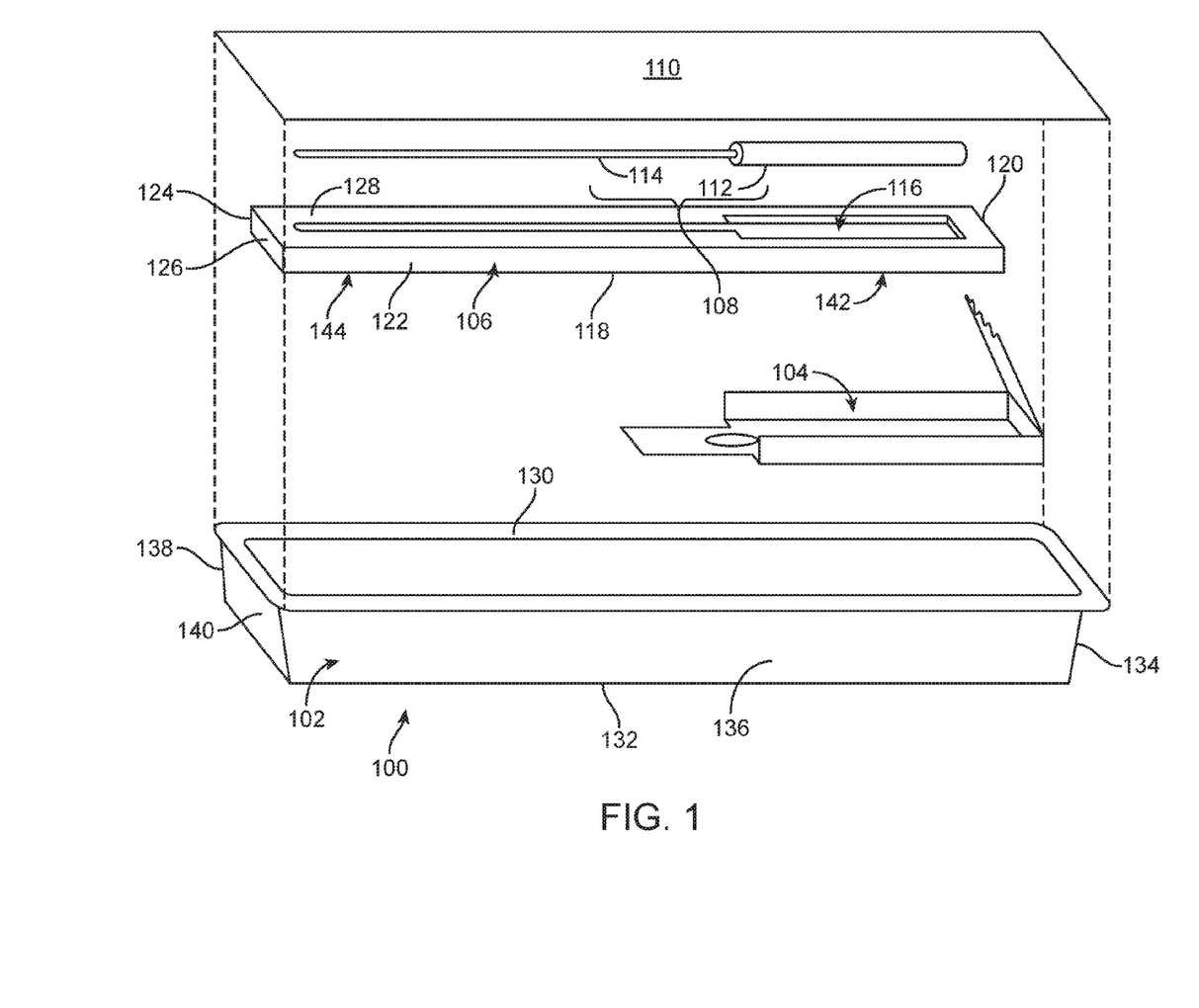
FIG. 1 is an exploded perspective view of a catheter delivery system package in accordance with one embodiment.

FIG. 1 is an exploded perspective view of a catheter delivery system package 100 in accordance with one embodiment. Referring to FIG. 1, catheter delivery system package 100 includes an outer tray 102, a slip card 104, an inner tray 106, a delivery system 108, and a lid 110. Catheter delivery system package 100 is a sterile container package for a delivery system 108. Delivery system 108 include a handle 112 and a protruding portion 114 protruding from handle 112. Examples of delivery system 108 includes the Valiant™ Aortic Stent Graft System, the Micra™ Transcatheter Pacing System (TPS), and the EnVeo R delivery system, although other delivery systems are used in other embodiments.

In one embodiment, delivery system 108, e.g., a medical device, includes one or more stents, grafts, stent-grafts, transcatheter heart valves, or other endoluminal devices for delivery and implantation within a patient. Protruding portion 114, e.g., a delivery system catheter, is cylindrical in accordance with one embodiment and is configured to be inserted into a patient. Protruding portion 114 is not limited to a cylindrical member and can take various shapes and have various features in accordance with other embodiments.

Inner tray 106 includes a delivery system opening 116 therein into which delivery system 108 is contained. Generally, delivery system opening 116 is complementary in shape to delivery system 108. In one embodiment, inner tray 106 includes various delivery system holding features for holding delivery system 108. For example, delivery system 108 is press fit into delivery system opening 116, which provides a variable interference fit for holding delivery system 108. In one embodiment, delivery system 108 is snapped into delivery system opening 116 and held therein.

Inner tray 106 is a ridged tray in accordance with one embodiment. Inner tray 106 includes a bottom 118, a proximal end 120, sides 122, 124, a distal end 126, and a top 128. Sides 122, 124 and ends 120, 126 extend upward and away from bottom 118 to top 128. Sides 122, 124 extend opposite one another and between proximal end 120 and distal end 126. Similarly, proximal end 120 and distal end 126 extend opposite one another and between sides 122, 124. Delivery system opening 116 is formed in top 128 in this embodiment.

Outer tray 102 includes an integral lid sealing flange 130 for sealing with lid 110. Outer tray 102 contains slip card 104, inner tray 106, and delivery system 108 therein. In various embodiments, outer tray 102 is formed using injection molding, blow molding, or thermoformed. After slip card 104, inner tray 106, and delivery system 108 are placed in outer tray 102, the sterile barrier is created with the addition of lid 110, e.g., a sealed Tyvek or other film lid. Lid 110 is mounted to lid sealing flange 130.

Outer tray 102 includes a bottom surface 132, a proximal end 134, sides 136, 138, and a distal end 140. Sides 136, 138 and ends 134, 140 extend upward and away from bottom surface 132 to lid sealing flange 130. Sides 136, 138 extend opposite one another and between proximal end 134 and distal end 140. Similarly, proximal end 134 and distal end 140 extend opposite one another and between sides 136, 138. Outer tray 102 and inner tray 106 are generally rectangular in this embodiment although have other shapes in other embodiments. In various embodiments, outer tray 102 and/or inner tray 106 are "U" shaped, expand outward from the bottom, expand downward and outward from lid sealing flange 130, are single walled, double walled, or have other shapes, e.g., depending upon the particular application.

As used herein, the distal end of delivery system 108 is identified as the end that is farthest from handle 112 while the proximal end of delivery system 108 is the end nearest handle 112. As used herein, the distal end of catheter delivery system package 100 including outer tray 102 and inner tray 106 is identified to the end that is farthest from handle 112 while the proximal end of catheter delivery system package 100 including outer tray 102 and inner tray 106 is the end nearest handle 112. Further, although various features may be referred to as top, bottom, and having other orientations, the features are relative to one another and are not gravitationally orientated. In addition, although various features may be referred to as planar, parallel, or perpendicular, the features may not exactly planar, parallel, or perpendicular, but only substantially planar, parallel, or perpendicular.

Figure 2:
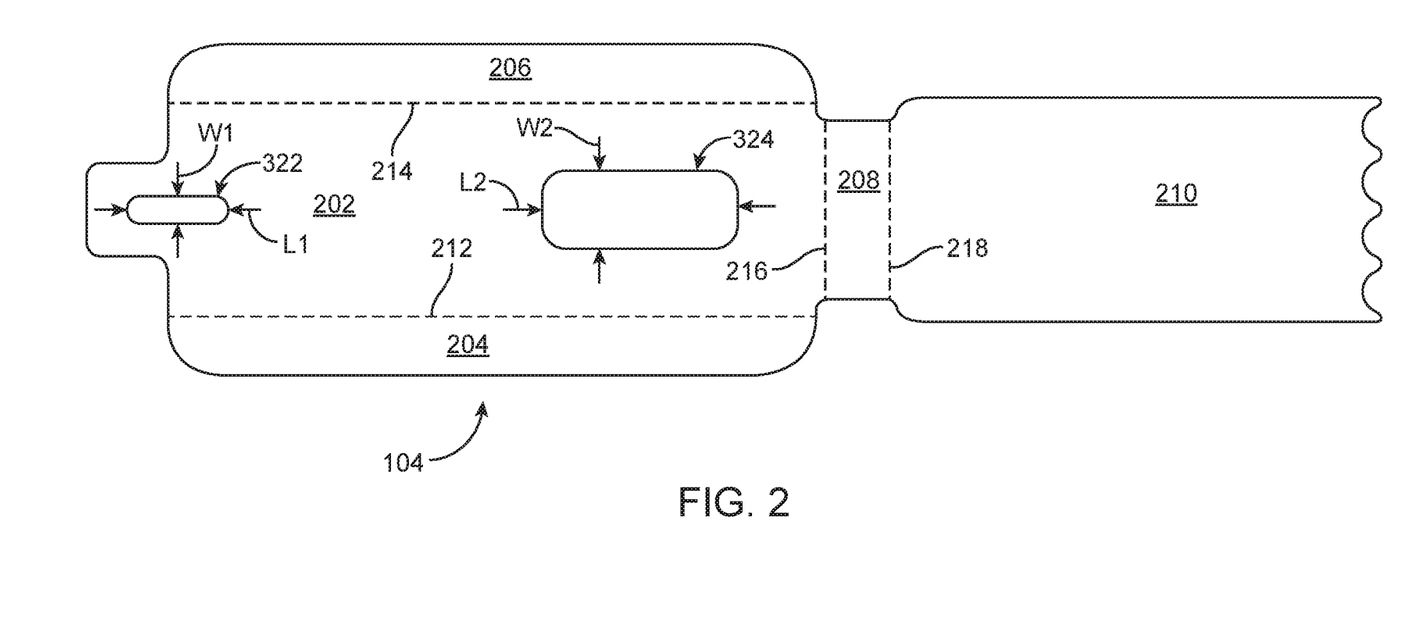
FIG. 2 is a laid out plan view of a slip card of the catheter delivery system package of FIG. 1 in accordance with one embodiment.

FIG. 2 is a laid out plan view of slip card 104 of catheter delivery system package 100 of FIG. 1 in accordance with one embodiment. As illustrated in FIG. 2, slip card 104 includes a base 202, sidewalls 204, 206, a pull tab connection flap 208, and a pull tab 210. In FIG. 2, a dashed line indicates a fold line. Base 202, sidewalls 204, 206, pull tab connection flap 208, and pull tab 210 are planar rigid surfaces in accordance with one embodiment. In one embodiment, slip card 104 is a die cut High Density Poly-Ethylene (HDPE) or other material card and can include hand grips for easy removal.

A fold in the lengthwise direction parallel to the longitudinal axis of delivery system 108 and the length of outer tray 102 is hereinafter referred to as a lengthwise fold. A fold in the sideways direction perpendicular to the lengthwise direction and parallel to the radial direction of delivery system 108 and the width of outer tray 102 is hereinafter referred to as a sideway fold. In light of this disclosure, it is to be understood that the folds may not be exactly straight and may not be exactly parallel or perpendicular to the length of outer tray 102. In one embodiment, a fold line includes internal cuts to allow slip card 104 to bend.

Sidewall 204 is connected to base 202 by a lengthwise sidewall fold 212. Sidewall 206 is connected to base 202 by a lengthwise sidewall fold 214. Pull tab connection flap 208 is connected to base 202 by a sideways pull tab connection flap fold 216. Pull tab 210 is connected to pull tab connection flap 208 by a sideways pull tab fold 218.

Figure 3:
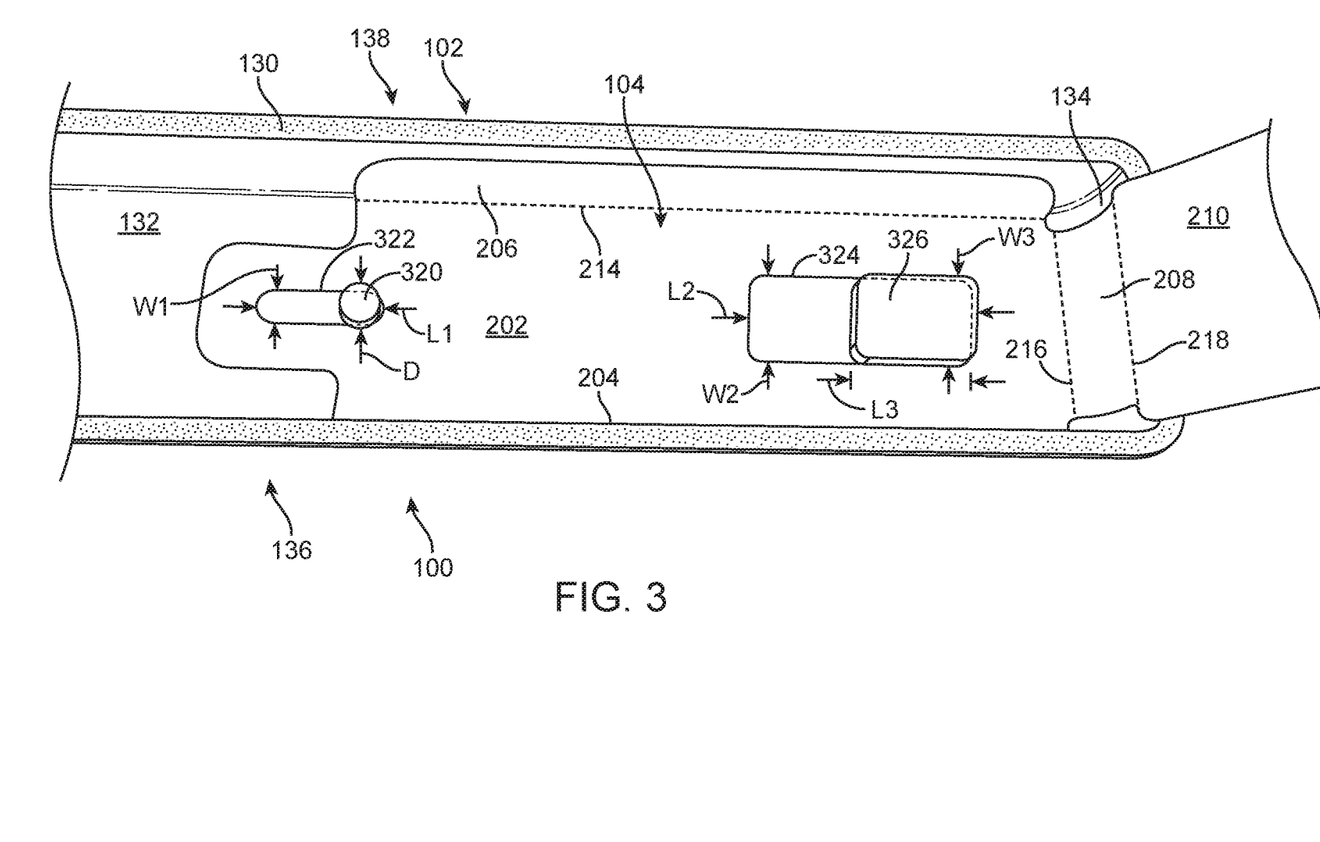
FIG. 3 is a perspective view of the slip card mounted within an outer tray of the catheter delivery system package prior to insertion of an inner tray of FIG. 1 in accordance with one embodiment.

FIG. 3 is a perspective view of slip card 104 mounted within outer tray 102 of catheter delivery system package 100 prior to insertion of inner tray 106 of FIG. 1 in accordance with one embodiment. Slip card 104 is placed within outer tray 102 such that base 202 of slip card 104 rests on and abuts bottom surface 132 of outer tray 102. Sidewalls 204, 206 are folded from base 202 at sidewall folds 212, 214 to be directly adjacent to and abut sides 136, 138 of outer tray 102, respectively. Pull tab connection flap 208 is folded from base 202 at pull tab connection flap fold 216 to be directly adjacent to and abut proximal end 134 of outer tray 102. Pull tab 210 is shown in a partially open position in FIG. 3. When loaded within outer tray 102, pull tab 210 is folded from pull tab connection flap 208 at pull tab fold 218 to be parallel to base 202 and slightly recessed below lid sealing flange 130 (see FIG. 5).

Figure 4:
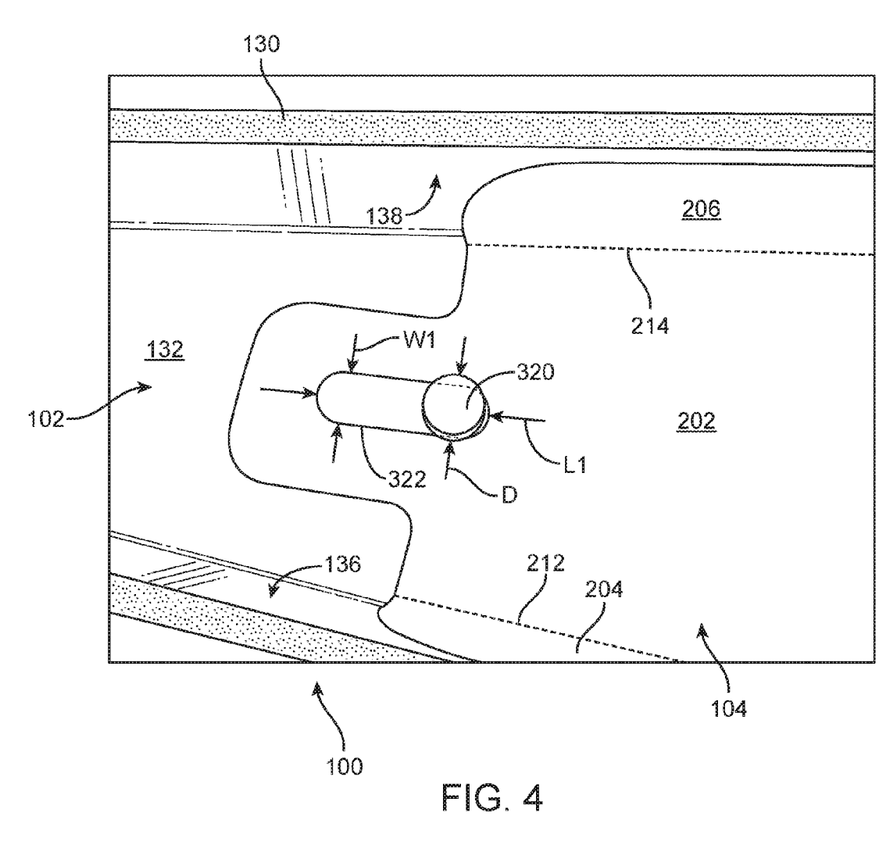
FIG. 4 is an enlarged perspective view of a slip card retaining feature of the outer tray within a slip card mounting slot of the slip card in accordance with one embodiment.

FIG. 4 is an enlarged perspective view of a slip card retaining feature 320 of outer tray 102 within a slip card mounting slot 322 of slip card 104 in accordance with one embodiment. Referring to FIGS. 2, 3, and 4 together, outer tray 102 includes slip card retaining feature 320 protruding upward from bottom surface 132 of outer tray 102. Slip card retaining feature 320 is a knob that has a small undercut and fits within slip card mounting slot 322 within base 202 of slip card 104.

Slip card mounting slot 322 has a length L1 and a width W1 and is located at the distal end of slip card 104. Length L1 is greater than diameter D of slip card retaining feature 320 and width W1 is marginally smaller than diameter D of slip card retaining feature 320. Slip card retaining feature 320 has a small undercut into which slip card 104 fits to lock slip card 104 to slip card retaining feature 320.

As discussed further below, slip card 104 is pulled proximally to slide slip card retaining feature 320 along the length of slip card mounting slot 322. As slip card retaining feature 320 contacts the distal end of slip card mounting slot 322, slip card retaining feature 320 prevents further proximal motion of slip card 104. Specifically, slip card retaining feature 320 prevents slip card 104 from unintentionally being pulled out of outer tray 102, e.g., during removal of inner tray 106.

In one embodiment, referring to FIG. 3, slip card 104 further includes a slip card alignment slot 324. A slip card alignment feature 326 of outer tray 102 is within slip card alignment slot 324 of slip card 104. More particularly, outer tray 102 includes slip card alignment feature 326 protruding upward from bottom surface 132 of outer tray 102. Slip card alignment feature 326 is a rectangular block that fits within slip card alignment slot 324 within base 202 of slip card 104.

Slip card alignment slot 324 has a length L2 and a width W2 and is located at the proximal end of base 202 of slip card 104. Length L2 is greater than length L3 of slip card alignment feature 326 and width W2 is approximately equal to, but can be slightly larger, than width W3 of slip card alignment feature 326 allowing slip card alignment feature 326 to fit within slip card alignment slot 324. By fitting within slip card alignment slot 324, slip card alignment feature 326 insures alignment of slip card 104 within outer tray 102.

In one embodiment, slip card alignment feature 326 also prevents slip card 104 from being unintentionally removed from outer tray 102, e.g., during removal of inner tray 106. As set forth below, slip card 104 is pulled proximally to slide slip card alignment feature 326 along the length of slip card alignment slot 324. As slip card alignment feature 326 contacts the distal end of slip card alignment slot 324, slip card alignment feature 326 prevents further proximal motion of slip card 104. Specifically, slip card alignment feature 326 prevents slip card 104 from unintentionally being pulled out of outer tray 102.

However, in another embodiment, slip card 104 is pulled up such that slip card alignment feature 326 is pulled out of slip card alignment slot 324. In accordance with this embodiment, slip card retaining feature 320 remains within slip card mounting slot 322 to prevent unintentional removal of slip card 104 from outer tray 102.

In other embodiments, catheter delivery system package 100 is formed without slip card retaining feature 320 and slip card mounting slot 322 and/or without slip card alignment feature 326 and slip card alignment slot 324. In another embodiment, slip card 104 is designed to lock onto sides 136, 138 of outer tray 102 to prevent slip card 104 from being pulled out of outer tray 102 during sliding action of inner tray 106. In another embodiment, sidewalls 204, 206, sometimes called side flaps, have indents that act as stoppers during pulling action.

Figure 5:
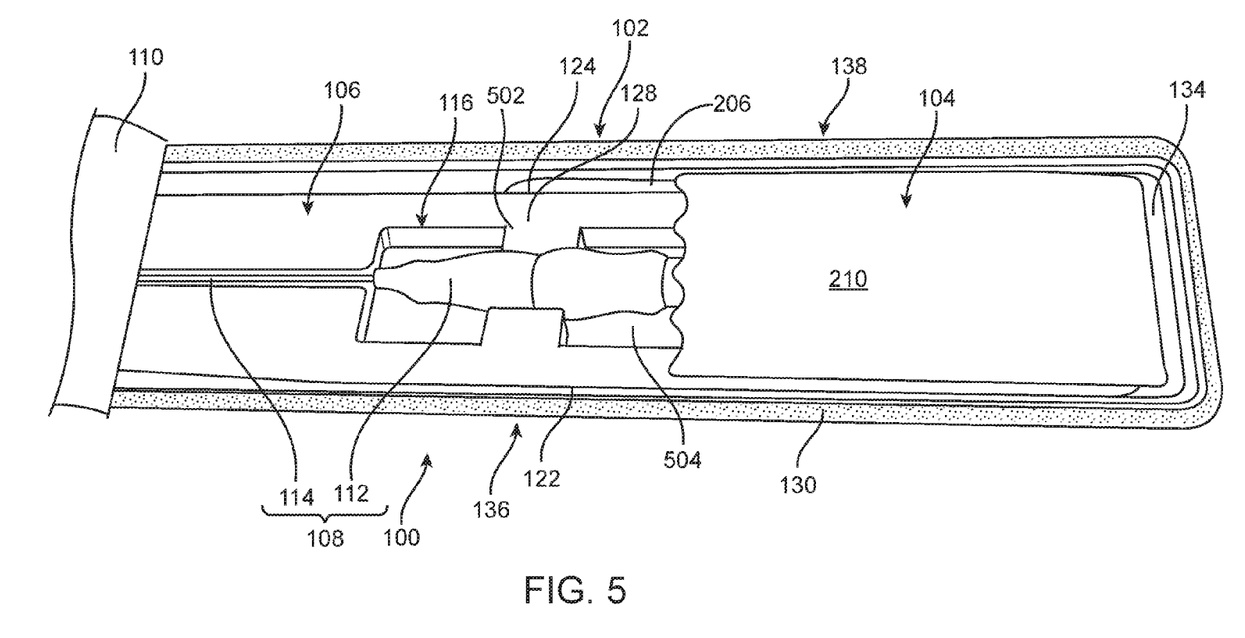
FIG. 5 is a perspective view of the catheter delivery system package having a lid partially removed to illustrate the slip card, the inner tray, and a delivery system in a loaded state within the outer tray in accordance with one embodiment.

FIG. 5 is a perspective view of catheter delivery system package 100 having lid 110 partially removed to illustrate slip card 104, inner tray 106, and delivery system 108 in a loaded state within outer tray 102 in accordance with one embodiment.

Slip card 104 is loaded into outer tray 102 as discussed above. Delivery system 108 is loaded within delivery system opening 116 in inner tray 106. In FIG. 5, delivery system holding features 502 are illustrated. Delivery system 108 is pressed between delivery system holding features 502, which provide a variable interference fit, to hold delivery system 108. Further, delivery system opening 116 includes enlarged areas 504 to allow easy grasping and removal of delivery system 108 from inner tray 106.

Referring to FIGS. 1, 3, and 5 together, inner tray 106 is placed on slip card 104 and within outer tray 102. More particularly, a proximal portion 142 of inner tray 106 is placed on base 202 of slip card 104. A distal portion 144 of inner tray 106 protrudes past slip card 104 to directly rest on outer tray 102.

Accordingly, base 202 of slip card 104 is between bottom 118 of inner tray 106 and bottom surface 132 of outer tray 102. Sidewalls 204, 206 of slip card 104 are between sides 122, 124 of inner tray 106 and sides 136, 138 of outer tray 102. Pull tab connection flap 208 is between proximal end 120 of inner tray 106 and proximal end 134 of outer tray 102. Pull tab 210 is between top 128 of inner tray 106 and lid 110. Generally, base 202, sidewalls 204, 206, and pull tab connection flap 208 are between delivery system 108 and bottom surface 132, sides 136, 138, and proximal end 134 of outer tray 102, respectively.

FIG. 5 is also representative of catheter delivery system package 100 during removal of inner tray 106 including delivery system 108. As illustrated in FIG. 5, to remove inner tray 106 including delivery system 108, the circulating nurse or other staff member partially or completely removes lid 110, e.g., by pulling and peeling lid 110 from outer tray 102.

Figure 6:
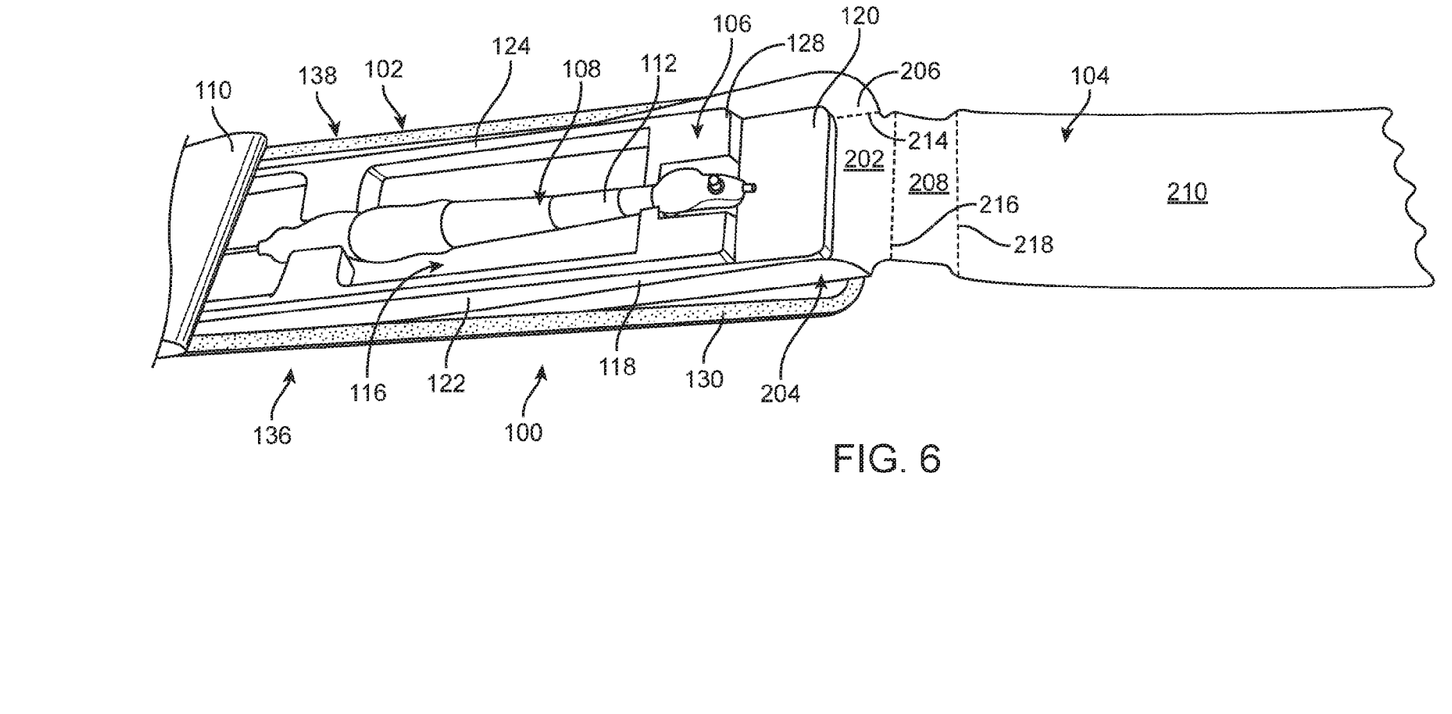
FIG. 6 is a perspective view of the catheter delivery system package of FIG. 5 at a later stage during removal of the inner tray including the delivery system in accordance with one embodiment.

FIG. 6 is a perspective view of catheter delivery system package 100 of FIG. 5 at a later stage during removal of inner tray 106 including delivery system 108 in accordance with one embodiment. As shown in FIG. 6, after partial or complete removal of lid 110 by the circulating nurse or other user, pull tab 210 is pulled by the scrub nurse or other staff member in the sterile field.

This raises slip card 104 including inner tray 106 and delivery system 108 from outer tray 102 at proximal end 134. At the same time, this moves pull tab connection flap 208 over lid sealing flange 130. Further, as sidewalls 204, 206 are raised above lid sealing flange 130, sidewall 204, 206 project outward and above lid sealing flange 130. Accordingly, slip card 104 extends over lid sealing flange 130 preventing contact between inner tray 106 and lid sealing flange 130. Lid sealing flange 130 is considered a non-sterile surface in accordance one embodiment and thus contact between inner tray 106 and lid sealing flange 130 must be prevented. Slip card 104 effectively forms a ramp for sterile removal of inner tray 106 from outer tray 102 as illustrated in FIG. 7.

Figure 7:
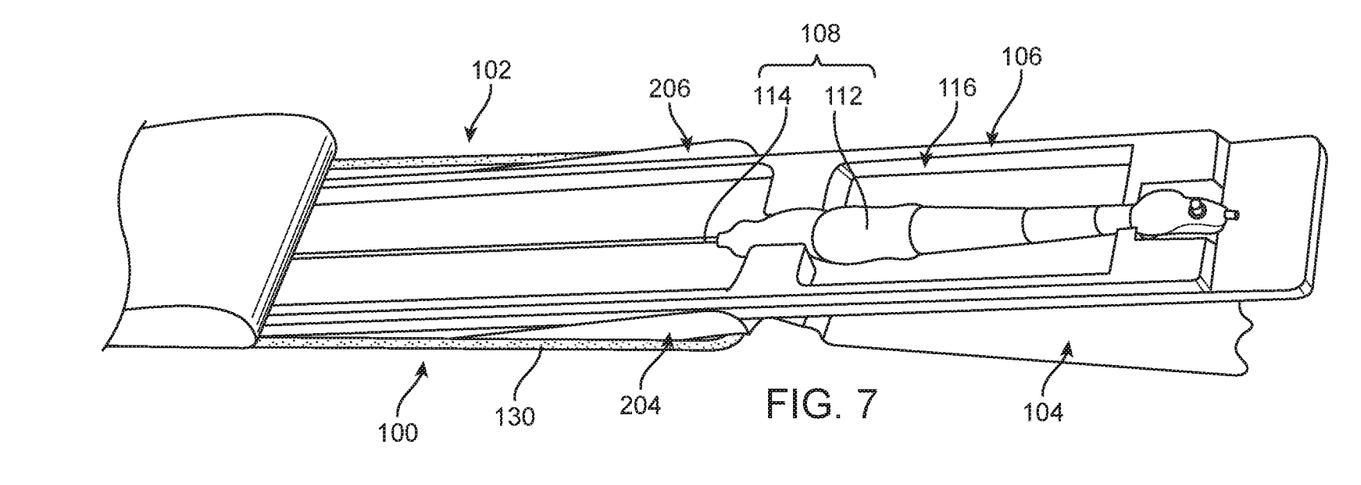
FIG. 7 is a perspective view of the catheter delivery system package of FIG. 6 at a later stage during removal of the inner tray including the delivery system in accordance with one embodiment.

FIG. 7 is a perspective view of catheter delivery system package 100 of FIG. 6 at a later stage during removal of inner tray 106 including delivery system 108 in accordance with one embodiment. Referring to FIG. 7, inner tray 106 is then grasped by the scrub nurse or other staff member in the sterile field and inner tray 106 including delivery system 108 is removed from catheter delivery system package 100.

Figure 8:
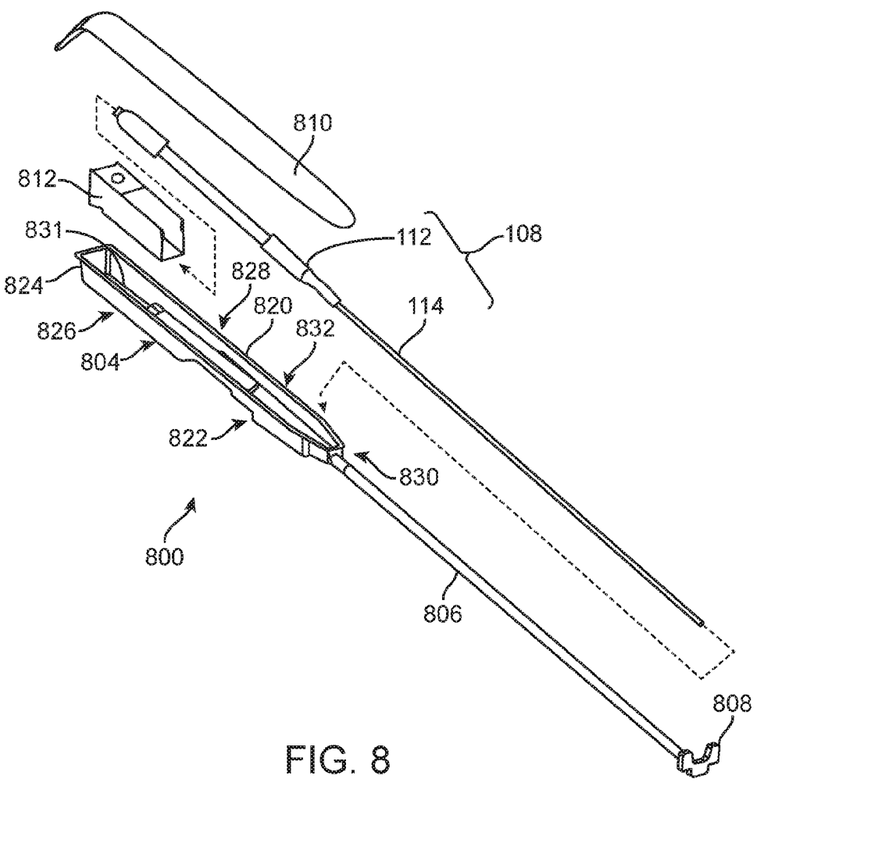
FIG. 8 is an exploded perspective view of a catheter delivery system package in accordance with another embodiment.

FIG. 8 is an exploded perspective view of catheter delivery system package 800 in accordance with another embodiment. Referring to FIG. 8, catheter delivery system package 800 includes a tray 804, an extension tube 806, an end cap 808, a lid 810, delivery system 108, and a slip card 812, sometimes called a device removal assist card. Catheter delivery system package 800 is a sterile container package for a delivery system 108. Tray 804, sometimes called a common injection-molded body, is a hybrid sealed tray in one embodiment. Tray 804 includes an integral lid sealing flange 820 for sealing with lid 810. Tray 804 contains handle 112 of delivery system 108 therein. In various embodiments, tray 804 is formed using injection molding, blow molding, or thermoformed. Examples of suitable trays are set forth in Barnell, U.S. patent application Ser. No. 15/277,509, filed Sep. 27, 2016 and Barnell, U.S. patent application Ser. No. 15/277,537, filed Sep. 27, 2016, which are both herein incorporated by reference in their entirety.

Tray 804 includes a bottom surface 822, a proximal end 824, sides 826, 828, and a distal end 830. Tray 804 further includes tray mounting slots 831 adjacent the intersection of bottom surface 822 and sides 826, 828 into which tray mounting surfaces of slip card 812 are inserted as discussed further below. Extension tube 806 is coupled to distal end 830 of tray 804. Sides 826, 828 and ends 824, 830 extend upward and away from bottom surface 822 to lid sealing flange 820. Sides 826, 828 extend opposite one another and between proximal end 824 and distal end 830. Similarly, proximal end 824 and distal end 830 extend opposite one another and between sides 826, 828.

End cap 808 hermetically seals the distal end of extension tube 806. Extension tube 806 in combination with tray 804 define a delivery system cavity 832 into which delivery system 108 is placed and sealed in a sterile condition. Generally, delivery system cavity 832 is a sterile sealed cavity defined by tray 804, extension tube 806, end cap 808 and lid 810.

More particularly, protruding portion 114 is slid into extension tube 806 though tray 804. Protruding portion 114 is slid into extension tube 806 until handle 112 is located within tray 804. In one embodiment, tray 804 includes various delivery system holding features for holding delivery system 108. For example, delivery system 108 is press fit into tray 804, which provides a variable interference fit for holding delivery system 108. In one embodiment, delivery system 108 is snapped into tray 804 and held therein. Generally, delivery system 108 is placed within delivery system cavity 832.

After slip card 812 is fitted within tray mounting slots 831 and delivery system 108 is placed in tray 804 and extension tube 806, the sterile barrier is created with the addition of lid 810, e.g., a sealed Tyvek or other film lid.

Figure 9:
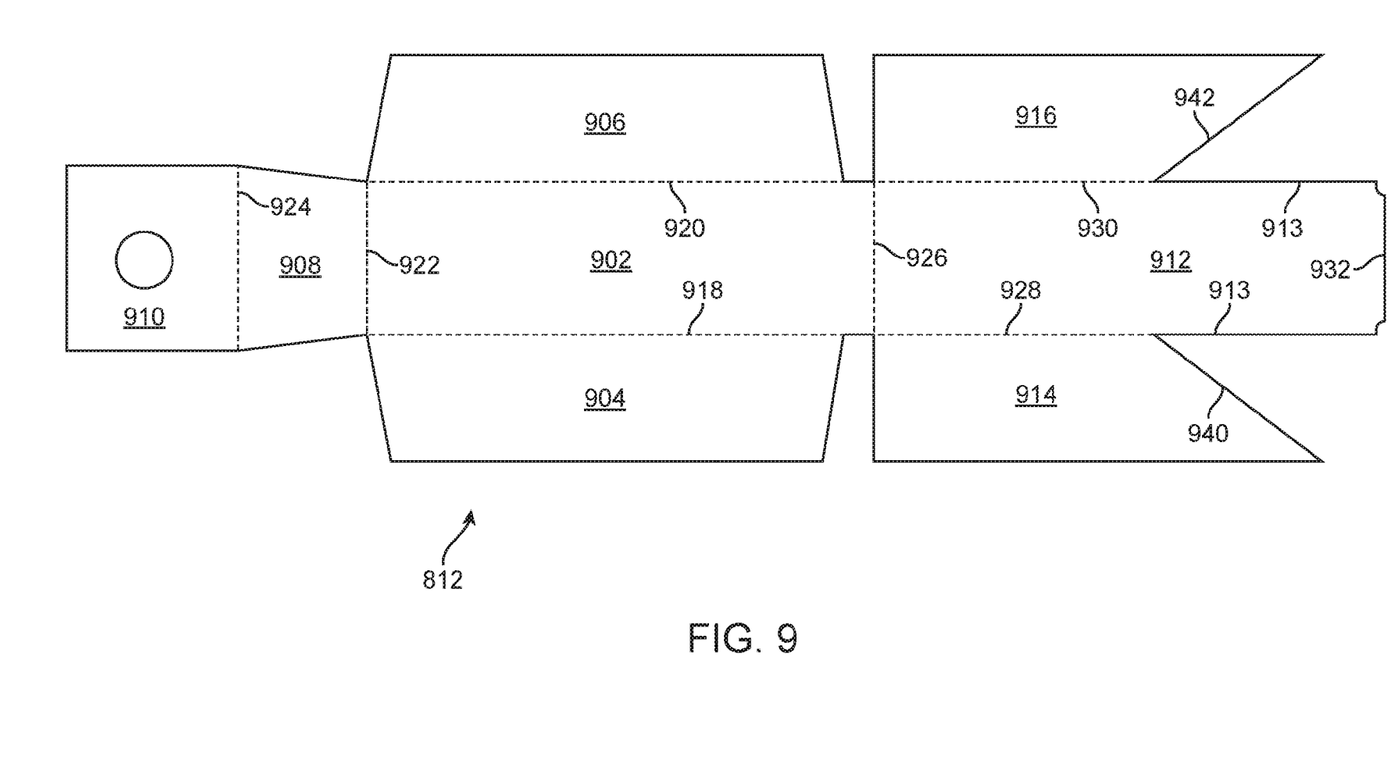
FIG. 9 is a laid out plan view of a slip card of the catheter delivery system package of FIG. 8 in accordance with one embodiment.

FIG. 9 is a laid out plan view of slip card 812 of catheter delivery system package 800 of FIG. 8 in accordance with one embodiment. As is illustrated in FIG. 9, slip card 812 includes a base 902, sidewalls 904, 906, a pull tab connection flap 908, a pull tab 910, a pivot flap 912 having tray mounting surfaces 913, and pivot flap sidewalls 914, 916. Base 902, sidewalls 904, 906, pull tab connection flap 908, pull tab 910, pivot flap 912 and pivot flap sidewalls 914, 916 are planar rigid surfaces in accordance with one embodiment. Tray mounting surfaces 913 are fitted within tray mounting slots 831 to permanently mate slip card 812 with tray 804.

Sidewall 904 is connected to base 902 by a lengthwise sidewall fold 918. Sidewall 906 is connected to base 902 by a lengthwise sidewall fold 920. Pull tab connection flap 908 is connected to base 902 by a sideways pull tab connection flap fold 922. Pull tab 910 is connected to pull tab connection flap 908 by a sideways pull tab fold 924. Pivot flap 912 is connected to base 902 by a sideways pivot flap fold 926. Pivot flap sidewalls 914, 916 are connect to pivot flap 912 by lengthwise pivot flap sidewall folds 928, 930.

Figure 10:
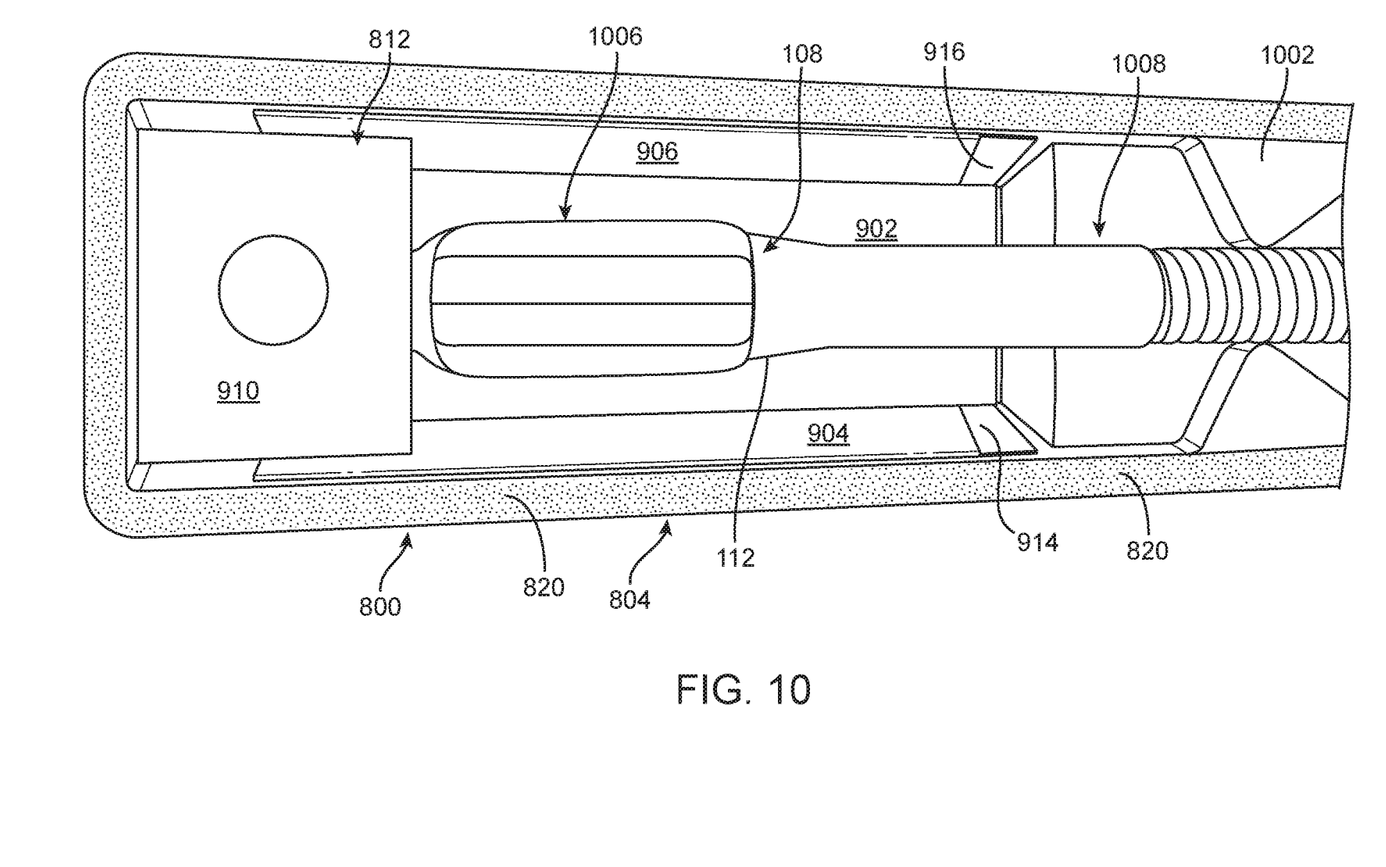
FIG. 10 is a perspective view of the catheter delivery system package of FIG. 8 having a lid removed to illustrate the slip card and a delivery system in a loaded state within a tray in accordance with one embodiment.

FIG. 10 is a perspective view of catheter delivery system package 800 of FIG. 8 having lid 810 removed to illustrate slip card 812 and delivery system 108 in a loaded state within tray 804 in accordance with one embodiment.

Referring to FIGS. 8, 9, and 10 together, slip card 812 is placed within tray 804 such that pivot flap 912 is folded at pivot flap fold 926 under base 902 and rests on and abuts bottom surface 822 of tray 804. A proximal end 932 of pivot flap 912 abuts and is held in place by proximal end 824 of tray 804. Pivot flap sidewalls 914, 916 are folded at pivot flap sidewall folds 928, 930 from pivot flap 912 to be adjacent to and abut sides 826, 828 of tray 804.

Base 902 abuts and rests on pivot flap 912. Sidewalls 904, 906 are folded at sidewall folds 918, 920 from base 902 to be directly adjacent to and abut pivot flap sidewalls 914, 916. Pivot flap sidewalls 914, 916 are between sidewalls 904, 906 and sides 826, 282 of tray 804.

Pull tab connection flap 908 is folded at pull tab connection flap fold 922 from base 902 to be directly adjacent to and abut proximal end 824 of tray 804. When loaded within tray 804, pull tab 910 is folded from pull tab connection flap 908 at pull tab fold 924 to be parallel to base 902 and slightly recessed below lid sealing flange 820.

Delivery system 108 is loaded within delivery system cavity 832 in tray 804. In FIG. 10, delivery system holding features 1002 of tray 804 are illustrated. Delivery system 108 is pressed between delivery system holding features 1002, which provide a variable interference fit, to hold delivery system 108.

Delivery system 108 is placed on slip card 812 and within tray 804. More particularly, a proximal portion 1006 of handle 112 is placed on base 902 of slip card 812. A distal portion 1008 of handle 112 protrudes past slip card 812 to directly contact tray 804.

Accordingly, base 902 of slip card 812 is between handle 112 and bottom surface 822 of tray 804. Sidewalls 904, 906, and pivot flap sidewalls 914, 916 of slip card 812 are between handle 112 and sides 826, 828 of tray 804. Pull tab connection flap 908 is between handle 112 and proximal end 824 of tray 804. Pull tab 910 is between handle 112 and lid 810. Generally, base 902, sidewalls 904, 906, 914, 916, and pull tab connection flap 908 are between delivery system 108 and bottom surface 822, sides 826, 828, and proximal end 824 of tray 804, respectively.

FIG. 10 is also representative of catheter delivery system package 800 during removal of delivery system 108. As illustrated in FIG. 10, to remove delivery system 108, the circulating nurse or other staff member partially or completely removes lid 810, e.g., by pulling and peeling lid 810 from tray 804.

Figure 11:
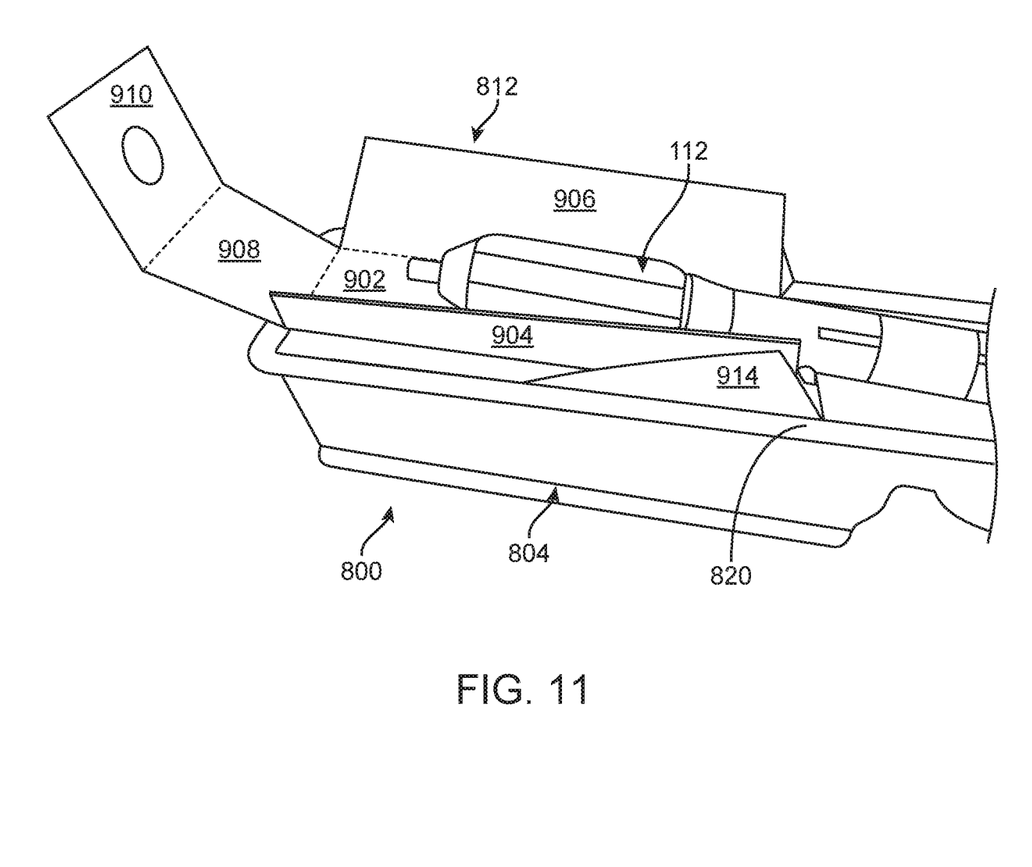
FIG. 11 is a perspective view of the catheter delivery system package of FIG. 10 at a later stage during removal of the delivery system in accordance with one embodiment.

FIG. 11 is a perspective view of catheter delivery system package 800 of FIG. 10 at a later stage during removal of delivery system 108 in accordance with one embodiment. As shown in FIG. 11, after partial or complete removal of lid 810 by the circulating nurse or other user, pull tab 910 is pulled by the scrub nurse or other staff member in the sterile field.

This raises slip card 812 including handle 112 of delivery system 108 from tray 804 at proximal end 824. At the same time, this moves pull tab connection flap 908 over lid sealing flange 820. Further, as sidewalls 904, 906 are raised above lid sealing flange 820, sidewalls 904, 906 project outward and above lid sealing flange 820. Accordingly, slip card 812 extends over lid sealing flange 820 preventing contact between delivery system 108 and lid sealing flange 820. Lid sealing flange 820 is considered a non-sterile surface in accordance one embodiment and thus contact between delivery system 108 and lid sealing flange 820 must be prevented. Slip card 812 effectively forms a ramp for sterile removal of delivery system 108 from tray 804 as illustrated in FIG. 11.

Further, in accordance with this embodiment, as pull tab 910 is proximally pulled, pivot flap fold 926 and generally the distal end of base 902 is proximally moved. As proximal end 932 of pivot flap 912 abuts and is held in place by proximal end 824 of tray 804, pivot flap fold 926 and generally the distal end of base 902 is raised from tray 804 thus raising handle 112. As illustrated in FIG. 9, pivot flap sidewalls 914, 916 include tapered edges 940, 942 rotating around pivot flap fold 926. Tapered edges 940, 942 make contact with bottom surface 822 of tray 804 thus defining the maximum height that base 902 lifts handle 112. In the above manner, handle 112 is raised thus allowing easy access to handle 112.

Handle 112 is then grasped by the scrub nurse or other staff member in the sterile field and handle 112 including delivery system 108 is removed from catheter delivery system package 800.

Figure 12:
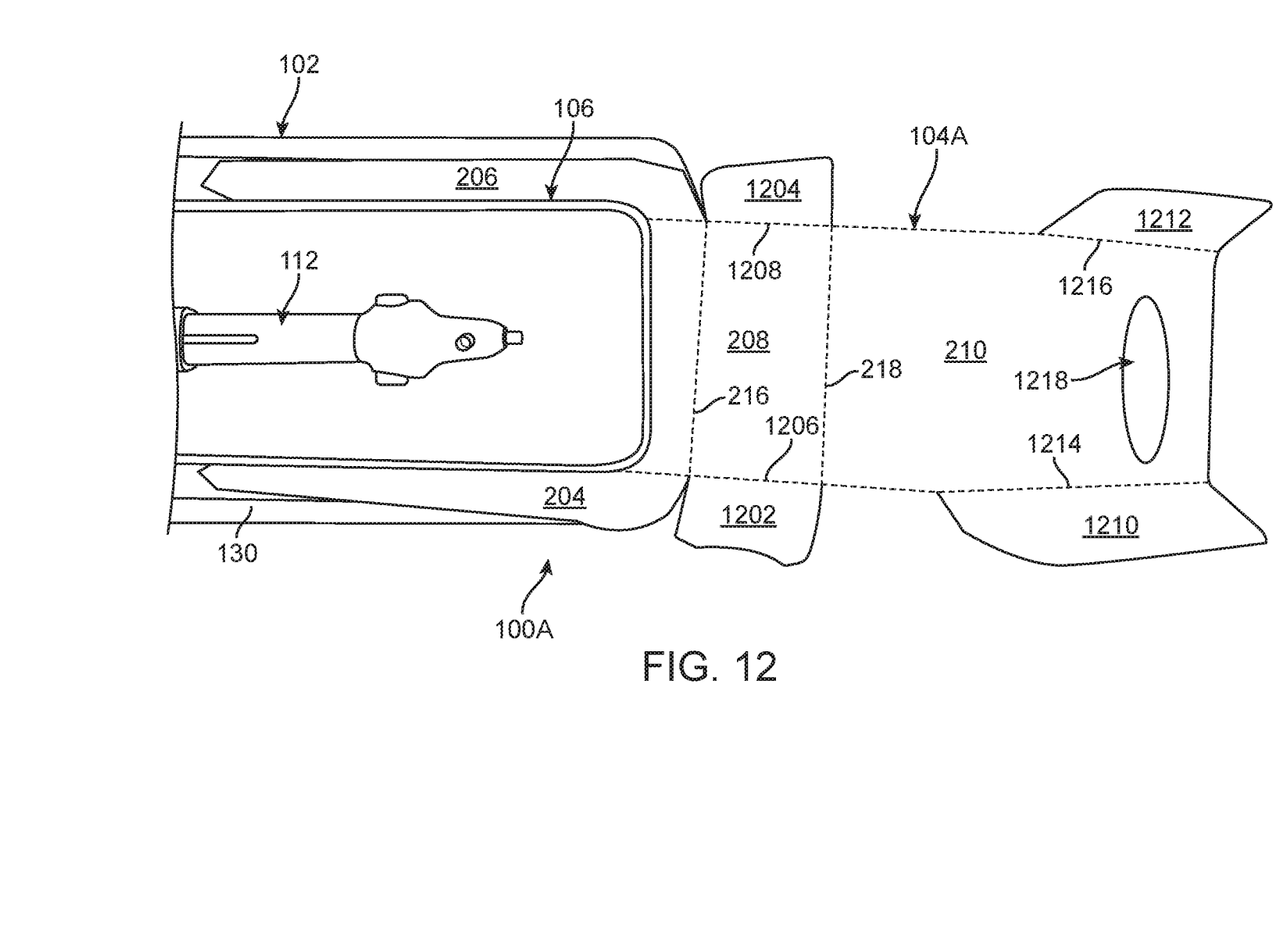
FIG. 12 illustrates a catheter delivery system package including a slip card in accordance with another embodiment.

FIG. 12 illustrates a catheter delivery system package 100A including a slip card 104A in accordance with another embodiment. Catheter delivery system package 100A including slip card 104A of FIG. 12 are similar to catheter delivery system package 100 including slip card 104 of FIGS. 2-7. Only the significant differences between catheter delivery system package 100A and slip card 104A of FIG. 12 and catheter delivery system package 100 and slip card 104 of FIGS. 2-7 are discussed below.

Referring now to FIG. 12, slip card 104A further includes corner flaps 1202, 1204 coupled to pull tab connection flap 208 by lengthwise corner flap folds 1206, 1208. Further, slip card 104A includes pull tab flaps 1210, 1212 coupled to pull tab 210 by lengthwise pull tab flap folds 1214, 1216. In one embodiment, pull tab 210 includes an opening 1218 therein, providing a handgrip. Flaps 1202, 1204, 1210, 1212 provide additional protection from contact with lid sealing flange 130 in one embodiment.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A packaging assembly comprising:
   an outer tray comprising:
      a bottom surface;
      a lid sealing flange;
      a first side extending between the bottom surface and the lid sealing flange;
      a second side extending between the bottom surface and the lid sealing flange;
   a delivery system;
   an inner tray, the delivery system being contained by the inner tray; and
   a slip card between the inner tray and the bottom surface, the first side and the second side, the inner tray being placed on the slip card and within the outer tray, wherein the slip card comprises:
      a base between a bottom of the inner tray and the bottom surface;
      a first side flap extending from the base and being adjacent the first side, the first side flap being between the first side and the inner tray;
      a second side flap extending from the base and being adjacent the second side, the second side flap being between the second side and the inner tray; and
      a pull tab coupled to the base, wherein the pull tab is parallel to the base.

2. The packaging assembly of claim 1 wherein the slip card further comprises:
   a pull tab connection flap coupling the pull tab to the base.

3. The packaging assembly of claim 2 wherein the outer tray further comprises a proximal end, the pull tab connection flap extending along the proximal end.

4. The packaging assembly of claim 1 further comprising a lid coupled to the lid sealing flange.

5. A packaging assembly comprising:
   an outer tray comprising:
      a bottom surface;
      a lid sealing flange;
      a first side extending between the bottom surface and the lid sealing flange; and
      a second side extending between the bottom surface and the lid sealing flange;
   a lid coupled to the lid sealing flange of the outer tray to define a cavity therein;
   a delivery system;
   an inner tray within the cavity, the delivery system being contained by the inner tray; and
   a slip card between the inner tray and the outer tray, the inner tray being placed on the slip card and within the outer tray, wherein the slip card comprises:
      a base between a bottom of the inner tray and the bottom surface;
      a first side flap extending and bendable from the base and adjacent the first side, the first side flap being between the first side and the inner tray; and
      a second side flap extending and bendable from the base and adjacent the second side, the second side flap being between the second side and the inner tray.

6. The packaging assembly of claim 5 wherein the base comprises a slip card mounting slot therein, the outer tray comprising a slip card retaining feature within the slip card mounting slot.

7. The packaging assembly of claim 6 wherein the slip card retaining feature protrudes from the bottom surface.

8. A method comprising:
   loading a delivery system within an inner tray;
   placing the inner tray on a slip card and within an outer tray, wherein a base of the slip card is between a bottom of the inner tray and a bottom surface of the outer tray;
   removing a lid from the outer tray to expose the inner tray within the outer tray; and
   moving a pull tab of the slip card away from the outer tray, wherein the moving of the pull tab moves the inner tray from the bottom surface of the outer tray and moves side flaps of the slip card to project outwards across a lid sealing flange of the outer tray.

9. The method of claim 8 further comprising removing the inner tray from the outer tray.

10. The method of claim 8 wherein the moving further comprises sliding the slip card along the bottom surface of the outer tray, the sliding comprises moving a slip card retaining feature protruding from the bottom surface of the outer tray within a slip card mounting slot of the slip card.

11. The method of claim 10 further comprising preventing removal of the slip card from the outer tray with the slip card retaining feature.

\* \* \* \* \*